US00PP27118P3

(12) United States Plant Patent
Bautista

(10) Patent No.: US PP27,118 P3
(45) Date of Patent: Aug. 30, 2016

(54) ***ECHEVERIA* PLANT NAMED 'BCEC-12.001'**

(50) Latin Name: ***Echeveria pulvinata* Rose**
Varietal Denomination: BCEC-12.001

(71) Applicant: Bay City Flower Company, Half Moon Bay, CA (US)

(72) Inventor: Rodolfo Valdoz Bautista, San Mateo, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 82 days.

(21) Appl. No.: 14/121,878

(22) Filed: Oct. 30, 2014

(65) Prior Publication Data

US 2016/0128259 P1 May 5, 2016

(51) Int. Cl.
*A01H 5/12* (2006.01)

(52) U.S. Cl.
USPC ..... Plt./373

(58) Field of Classification Search
USPC ..... Plt./373, 263.1, 372
See application file for complete search history.

*Primary Examiner* — Anne Grunberg
(74) *Attorney, Agent, or Firm* — James R. Cypher; Charles R. Cypher

(57) ABSTRACT

A plant variety of the *Echeveria* genus, having the varietal designation 'BCEC-12.001', with a spreading growth habit, showy appearance due to the color of the hairs on the apex and margin of its leaves. The plant does not flower.

3 Drawing Sheets

Latin name of genus and species of the plant claimed: *Echeveria pulvinata* Rose.

Varietal denomination: The new plant's varietal denomination is 'BCEC-12.001'.

BACKGROUND OF THE INVENTION

The present invention relates to a new and distinct variety of the Crassulaceae family, *Echeveria* genus. The new variety is named 'BCEC-12.001'.

SUMMARY OF THE INVENTION

The distinguishing characteristics of the new variety are retained by asexually reproduced, successive generations.

The plant was found by the inventor in a cultivated area of a commercial nursery where the inventor was growing *Echeveria pulvinata* Rose 'BCEC07.001'. *Echeveria pulvinata* Rose 'BCEC07.001' is the subject of U.S. Plant Pat. No. 24,559 P3, issued Jun. 17, 2014.

The new variety possesses the commercially desirable characteristics of: a spreading growth habit with dense, attractive foliage, and the plant does not flower. At the time the plant would normally bloom the hairs on the leaf margins at the apex, and sometimes also the hairs on the upper abaxial and adaxial leaf surfaces are R.H.S 59 B (red-purple group).

The new variety primarily differs from *Echeveria pulvinata* Rose 'BCEC07.001' by virtue of the fact that it does not flower. Also, the hair at the leaf tips and margins of the new variety is R.H.S. 59 B (red-velvet group). The leaf tips and margins of U.S. Plant Pat. No. 24,559 are also puberulent, however, the hair at the leaf tips and margins of U.S. Plant Pat. No. 24,559 is R.H.S. 44B (red-purple group).

The inventor has asexually reproduced the new variety through successive generations by cuttings at a commercial nursery in Half Moon Bay Calif., and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The pictured plant was grown in a 4 inch pot and lateral stems and leaves were removed or fell from the basal portions of the stems. The plants were also pinched to encourage lateral branching.

The following description is based on observations of optimally fertilized plants grown at a commercial nursery in Half Moon Bay, Calif. Temperatures in Half Moon Bay on average range from 55 to 65 degrees Fahrenheit in the summer months, and from 45 to 55 degrees Fahrenheit in the winter months.

DETAILED PLANT DESCRIPTION

Varietal name: 'BCEC-12.001'.

Classification:

*Family*.—Crassulaceae.

*Genus and species*.—*Echeveria pulvinata* Rose.

Form: Succulent, terrestrial plant. Relatively short rosulate primary stems with axilary branches. The observed plants were approximately 12.5 cm high and 20 cm in diameter. The longest axillary branches are approximately 10 cm in length.

Figure 1:
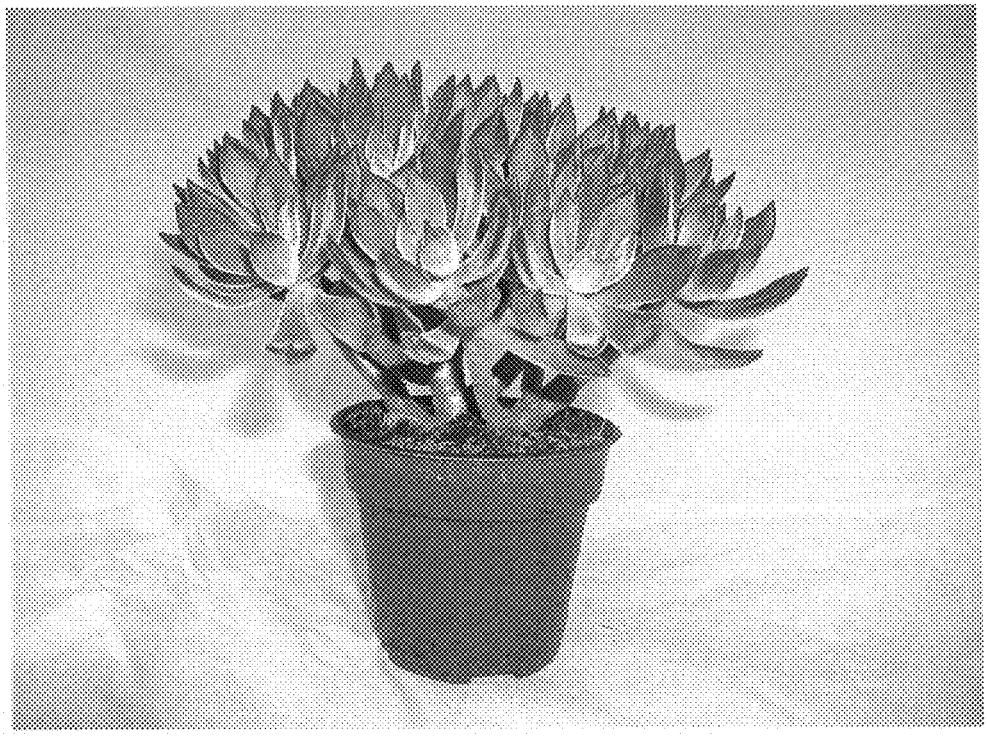
FIG. 1 is a color photograph of a plant grown from a cuttings of the new variety illustrating the overall appearance and form of the plant.
Figure 2:
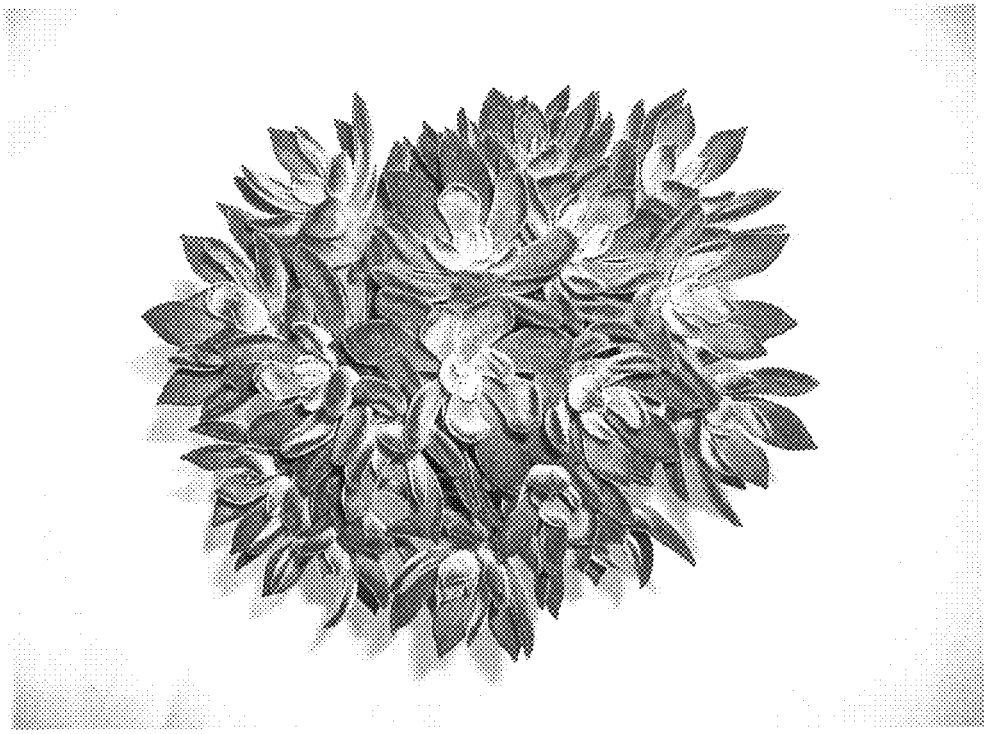
FIG. 2 is a color photograph of the plant showing the top of the plant.
Figure 3:
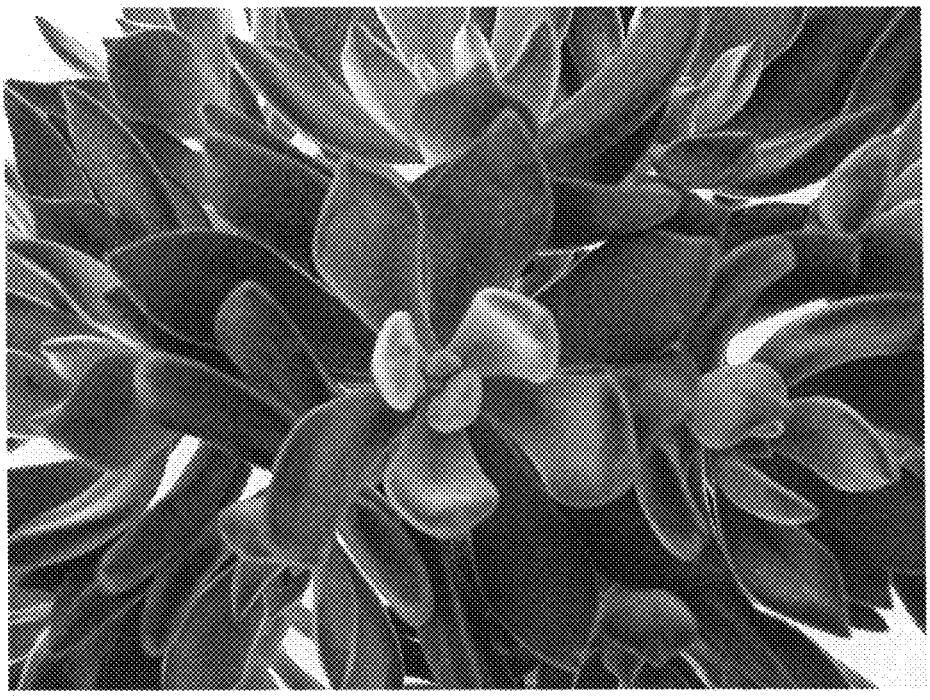
FIG. 3 is a color photograph of top of the plant, centered on the apex of a stem of the new variety.
Figure 4:
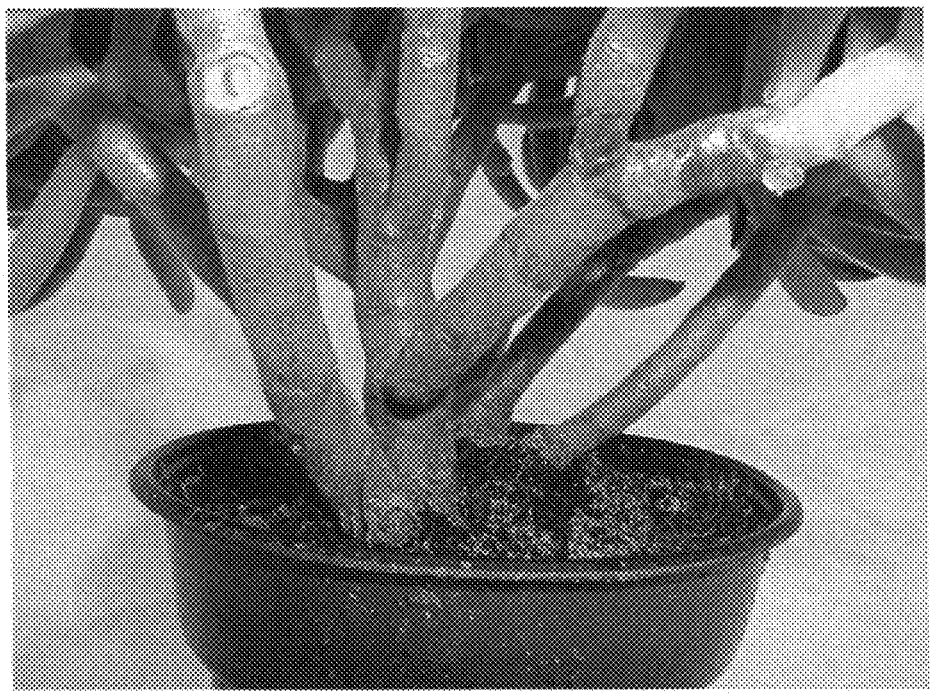
FIG. 4 is a color photograph of the base of the new variety.
Figure 5:
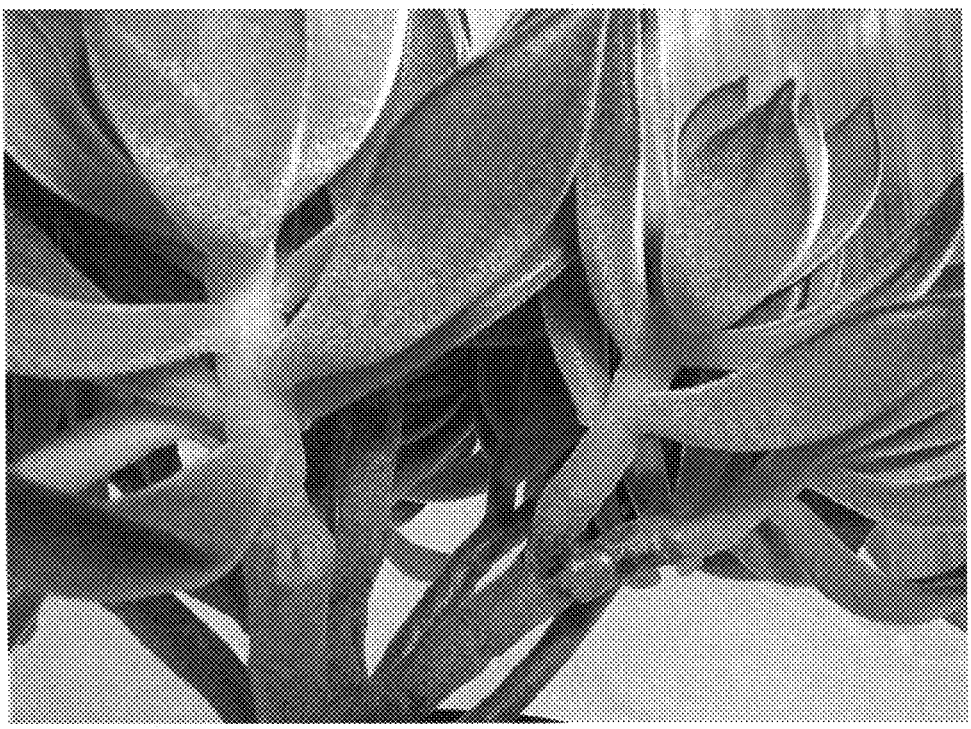
FIG. 5 is a color photograph of a stems of the new variety.
Figure 6:
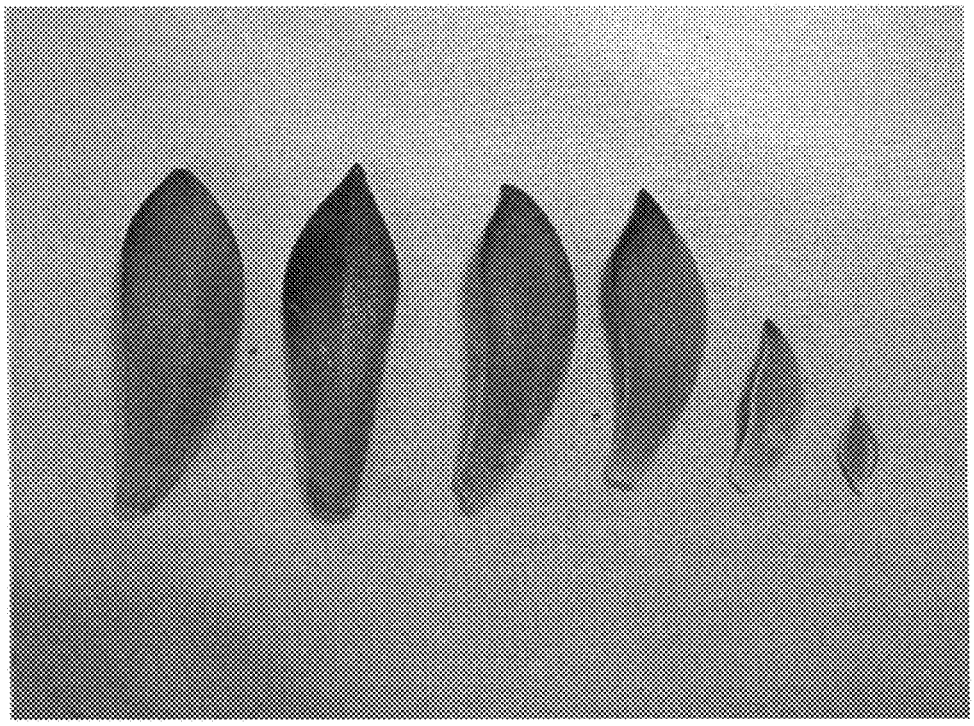
FIG. 6 is a color photograph of leaves of various sizes of the new variety, showing the adaxial surfaces.

Stems:

*General*.—Stems branch easily when pinched. Lateral branches are similar in length to the main stem with the plant having a uniform crown (see FIG. 1). Older basal stems are 1 cm in diameter and mostly devoid of leaves. Older leaves wither and fall off. Older basal stems are puberlent and R.H.S. 195 C (greyed-green group) with hairs that are R.H.S. 177 A (greyed-orange group). Young stem portions near their apex are R.H.S. 138 B (green group) and are densely pubescent with colorless hair. Stems are 5 mm in diameter below their apex.

Leaves:

*General*.—Leaves densely whorled, rosulate on primary and axillary stems. Leaves are simple, entire, fleshy and puberlent. They are oblanceolate to spatulate with broadly acuminate tips and have no petiole. Size of largest leaves: Length — 50 mm. Width — 20 mm wide. Thickness — 6 mm. Color: Adaxial and abaxial surfaces of leaves are predominately R.H.S. 138 B (green group). Hairs at leaf tips and margins are R.H.S. 59 B (red-purple group), and sometimes the upper abaxial and adaxial surfaces as well. Texture — Abaxial and adaxial surfaces of the leaves are puberlent. Hair on most of the abaxial and adaxial surfaces are colorless.

Fragrance: None.

I claim:

1. A new and distinct variety of *Echeveria* plant, substantially as herein shown and described.

* * * * *